(12) United States Patent
Do et al.

(10) Patent No.: US 11,009,392 B2
(45) Date of Patent: *May 18, 2021

(54) APPARATUS FOR MEASURING CIRCADIAN ILLUMINANCE

(71) Applicant: Kookmin University Industry Academy Cooperation Foundation, Seoul (KR)

(72) Inventors: Young Rag Do, Seoul (KR); Ji Hye Oh, Gyeonggi-do (KR)

(73) Assignee: KOOKMIN UNIVERSITY INDUSTRY ACADEMY COOPERATION FOUNDATION

( * ) Notice: Subject to any disclaimer, the term of this patent is extended or adjusted under 35 U.S.C. 154(b) by 0 days.

This patent is subject to a terminal disclaimer.

(21) Appl. No.: 16/511,065

(22) Filed: Jul. 15, 2019

(65) Prior Publication Data
US 2020/0018644 A1 Jan. 16, 2020

(30) Foreign Application Priority Data
Jul. 16, 2018 (KR) .................. 10-2018-0082323

(51) Int. Cl.
*G01J 1/44* (2006.01)
*G01J 1/04* (2006.01)
*A61B 5/00* (2006.01)

(52) U.S. Cl.
CPC ............. *G01J 1/44* (2013.01); *G01J 1/0492* (2013.01); *A61B 5/4857* (2013.01)

(58) Field of Classification Search
CPC ........ A61B 5/4857; G01J 1/0492; G01J 1/44; G01J 1/0488
See application file for complete search history.

(56) References Cited

U.S. PATENT DOCUMENTS

| | | | |
|---|---|---|---|
| 2008/0319354 A1* | 12/2008 | Bell | A61B 5/4812 600/595 |
| 2014/0131576 A1* | 5/2014 | Park | G01J 1/0492 250/338.1 |
| 2018/0094970 A1* | 4/2018 | Schneider | G01J 1/42 |
| 2020/0018640 A1* | 1/2020 | Bonitatibus | G01J 1/08 |
| 2020/0230346 A1* | 7/2020 | Mo | A61M 21/02 |

FOREIGN PATENT DOCUMENTS

| | | |
|---|---|---|
| JP | 2018-017516 A | 2/2018 |
| KR | 10-2015-0101179 A | 9/2015 |
| KR | 10-2015-0138385 A | 12/2015 |
| KR | 10-2017-0123065 A | 11/2017 |

* cited by examiner

*Primary Examiner* — Dominic J Bologna
(74) *Attorney, Agent, or Firm* — Harness, Dickey & Pierce, P.L.C.

(57) ABSTRACT

The present disclosure provides a circadian illuminance measuring apparatus including: a circadian lambda filter configured to pass external light according to a circadian sensitivity curve; a light sensor configured to sense the external light has passed through the circadian lambda filter, convert the external light into an analog signal, and output the analog signal; and a circadian illuminance calculator configured to convert the analog signal into a digital signal to calculate circadian illuminance of the external light.

11 Claims, 3 Drawing Sheets

APPARATUS FOR MEASURING CIRCADIAN ILLUMINANCE

CROSS-REFERENCE TO RELATED APPLICATION

This application claims priority to and the benefit of Korean Patent Application No. 2018-0082323, filed on Jul. 16, 2018, the disclosure of which is incorporated herein by reference in its entirety.

BACKGROUND

1. Field of the Invention

The present disclosure relates to a circadian illuminance measuring apparatus.

2. Discussion of Related Art

Humans live in a daily cycle known as a circadian rhythm, and the circadian rhythm is most affected by light.

When the sun rises in the morning, the sky begins to brighten, and as the sun sets, the sky darkens in the evening. According to such daily changes of the sun, various organisms have also changed and adapted over a long time, and humans are also affected by the daily changes of the sun and live in a daily cycle in which, when the sun rises in the morning, the humans get up and start their day, and in the evening when the sun sets, the humans rest and sleep.

Meanwhile, when the human body receives light in an evening time period, the secretion of melatonin, one hormone that has a great effect on sleep in the human body, is suppressed, which interferes with deep sleep and disturbs the circadian rhythm, thereby increasing the probability of exposure to various diseases.

Diseases caused by disturbance of the circadian rhythm include seasonal affective disorders, sleep disorders, depression, jet lag, and health problems associated with shift work, and in order to treat these diseases, it is necessary to balance the circadian rhythm by suppressing the secretion of melatonin in a morning time period and thus helping melatonin to be easily secreted in the evening time period.

Meanwhile, a general illuminance measuring apparatus measures the illuminance of external light using a visual lambda filter (v-λ Filter) that follows a visual sensitivity curve (v-λ), that is, a light sensitivity characteristic curve for human eyes.

Such a visual sensitivity curve has a maximum sensitivity in light having a wavelength band of about 550 nm to 600 nm.

However, in the general illuminance measuring apparatus following the visual sensitivity curve, different external light may have different circadian illuminance values according to the type of external light source even when the same illuminance value is measured. This is because a luminescence spectrum varies according to the type of external light source, and when the luminescence spectrum is changed, the light sensitivity characteristic of the hormones controlling the circadian rhythm changes.

For this reason, in order to measure the circadian illuminance, the conventional circadian illuminance measuring apparatus used a complicated method in which an illuminance value and a luminescence spectrum of the external light source were both measured, and then the circadian illuminance value was calculated based on the measured illuminance value and luminescence spectrum.

SUMMARY OF THE INVENTION

The present disclosure is directed to providing a circadian illuminance measuring apparatus capable of measuring circadian illuminance in a relatively simple manner by applying a circadian lambda filter, downsizing the apparatus by omitting additional components for calculating the circadian illuminance, and applying to various products at low cost.

The present disclosure is also directed to providing a circadian illuminance measuring apparatus capable of diagnosing a circadian rhythm of a user by measuring circadian illuminance, and reinforcing the circadian rhythm of the user according to the diagnosed circadian rhythm of the user.

The technical problems to be solved by the present disclosure is not limited to the above-described technical problems, and other technical problems which are not described can be clearly understood by those skilled in the art to which the present disclosure pertains from the following description.

According to an aspect of the present disclosure, there is provided a circadian illuminance measuring apparatus including: a circadian lambda filter configured to pass external light according to a circadian sensitivity curve; a light sensor configured to sense the external light has passed through the circadian lambda filter, convert the external light into an analog signal, and output the analog signal; and a circadian illuminance calculator configured to convert the analog signal into a digital signal to calculate circadian illuminance of the external light.

The circadian sensitivity curve may be a light sensitivity characteristic curve for a hormone that controls a circadian rhythm, and may be a curve having the maximum sensitivity in a circadian wavelength band.

The hormone that controls the circadian rhythm may be melatonin.

The circadian wavelength band may be in a range of 450 nm to 550 nm, a full-width at half-maximum transmission (FWHM) of the circadian wavelength band may in a range of 80 nm to 95 nm, and the circadian wavelength band may have an area concordance rate of 80% or more with a wavelength band of the circadian sensitivity curve.

The circadian lambda filter may be a band pass filter formed by cascading a blue pass filter and a yellow pass filter.

The circadian illuminance measuring apparatus may further include a display part configured to display the circadian illuminance corresponding to the digital signal.

The circadian illuminance calculator may include a programmable gain amplifier configured to receive the analog signal from the light sensor, amplify the analog signal, and output the amplified signal after varying an output gain.

The circadian illuminance calculator may further include an analog-digital converter configured to receive the analog signal amplified by the programmable gain amplifier, and convert the analog signal into the digital signal.

The output gain may be a gain value satisfying a range in which the analog signal received by the analog-digital converter is processed by the analog-digital converter.

The circadian illuminance calculator may further include a controller configured to output a control signal for varying the output gain to the programmable gain amplifier when the analog signal received by the analog-digital converter is out of the range in which the analog signal is processed by the analog-digital converter.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXAMPLE EMBODIMENTS

Figure 1:
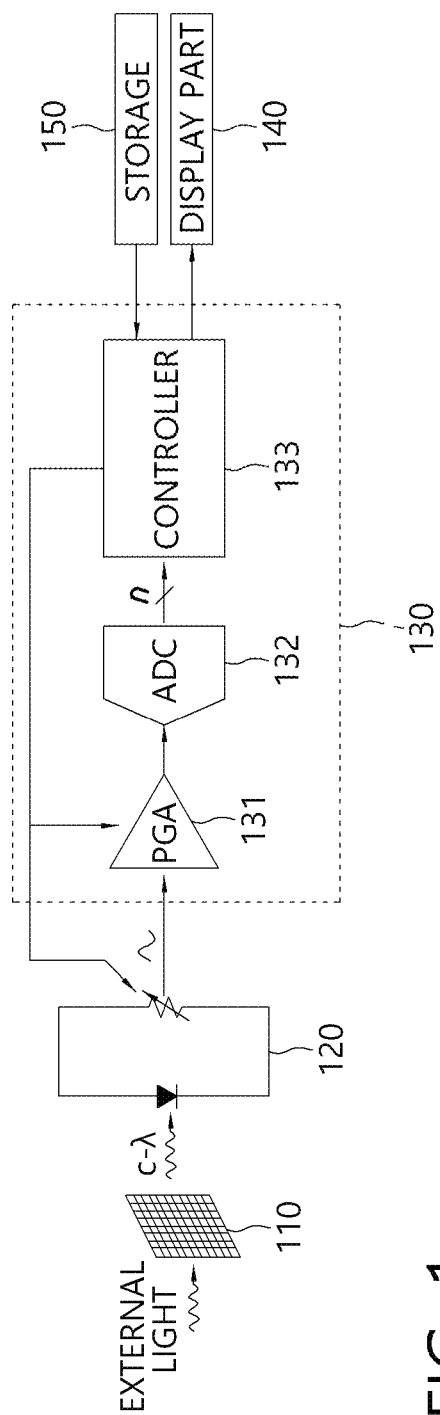
FIG. 1 is a schematic block diagram of a circadian illuminance measuring apparatus according to an embodiment of the present disclosure.

Exemplary embodiments of the present disclosure will be described in detail below with reference to the accompanying drawings. The same reference numerals are used for the same or similar elements regardless of the drawing number, and a redundant description thereof is omitted.

In the description of the present disclosure, if it is determined that a detailed description of commonly-used technologies or structures related to the disclosure may obscure the subject matter of the present disclosure, the detailed description is omitted. Further, the attached drawings are provided to easily understand the spirit of the present disclosure, and it should not be interpreted that the spirit of the present disclosure is limited by the attached drawings.

Figure 2:
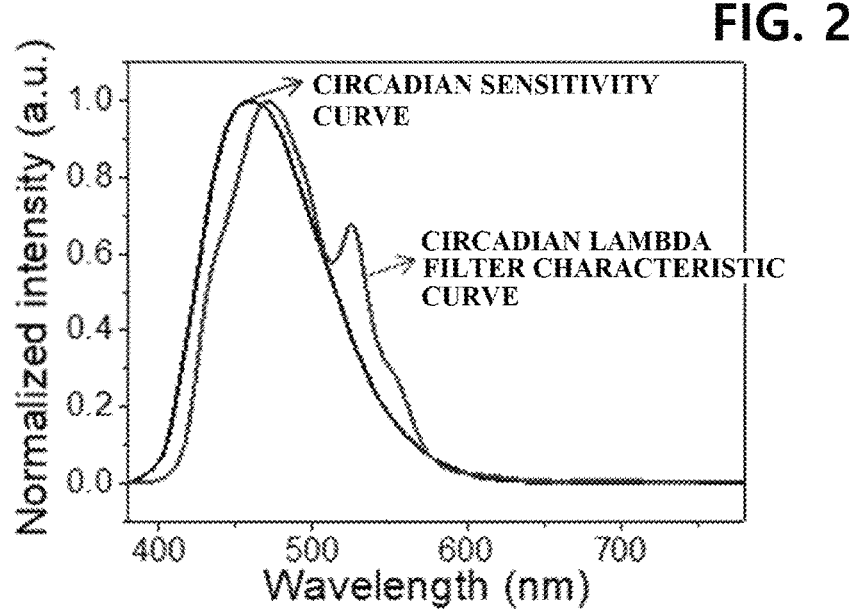
FIG. 2 is a graph illustrating a characteristic curve of a circadian lambda filter according to the embodiment of the present disclosure and a circadian sensitivity curve.
Figure 3:
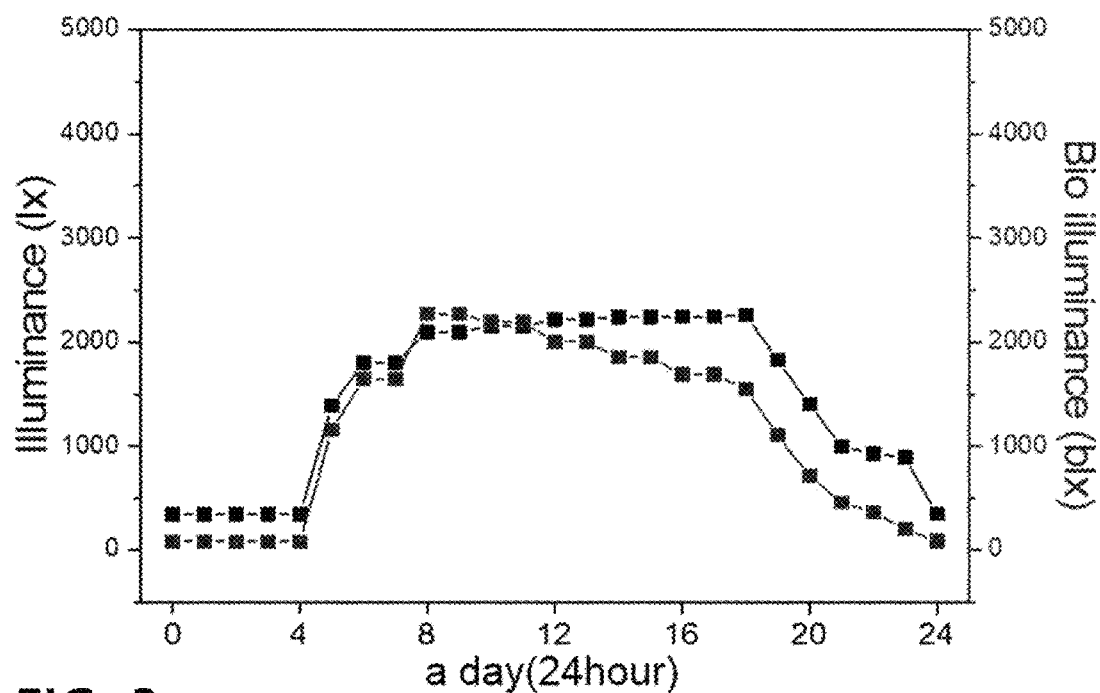
FIG. 3 is a graph illustrating the results of comparative measuring of illuminance and circadian illuminance of a circadian illumination for 24 hours.
Figure 4A:
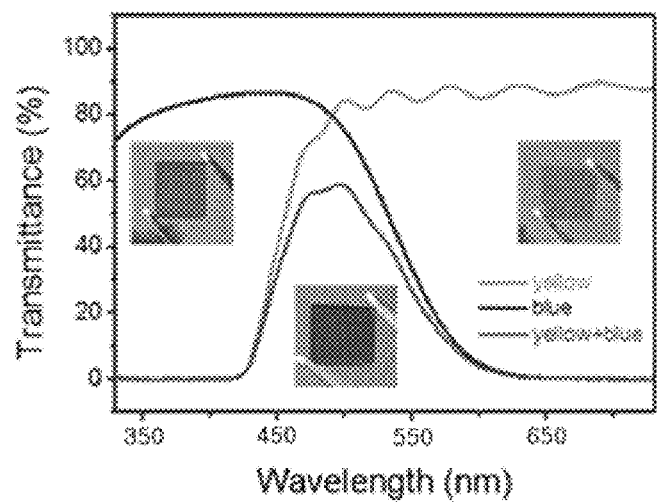
FIGS. 4A and 4B are graphs for describing the characteristics of the circadian lambda filter of FIG. 1.
Figure 4B:
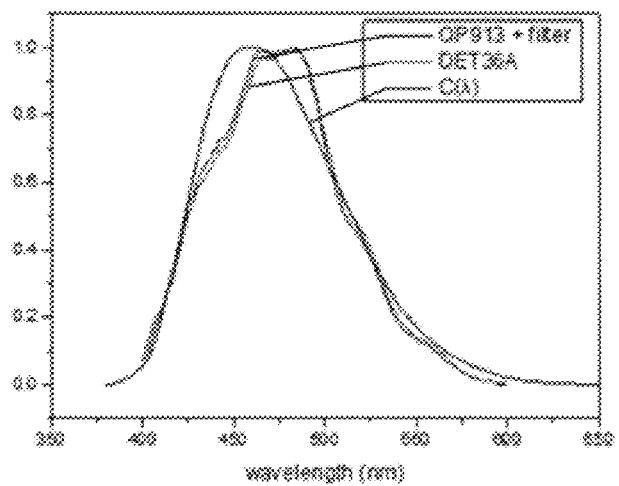

FIG. 1 is a schematic block diagram of a circadian illuminance measuring apparatus according to an embodiment of the present disclosure. FIG. 2 is a graph illustrating a characteristic curve of a circadian lambda filter according to the embodiment of the present disclosure and a circadian sensitivity curve. FIG. 3 is a graph illustrating the results of comparative measuring of illuminance and circadian illuminance of a circadian illumination for 24 hours. FIGS. 4A and 4B are graphs for describing the characteristics of the circadian lambda filter of FIG. 1.

As shown in FIG. 1, a circadian illuminance measuring apparatus 100 according to the embodiment of the present disclosure may include a circadian lambda filter (c-λ filter) 110, a light sensor 120, and a circadian illuminance calculator 130.

The circadian illuminance measuring apparatus 100 according to the embodiment of the present disclosure measures circadian illuminance (biolux) using the fact that hormones such as melatonin or cortisol, which control a circadian rhythm of a human, are related to light.

Specifically, the circadian lambda filter 110 passes the external light according to the circadian sensitivity curve (circadian lambda: c-λ).

Here, the circadian sensitivity curve is a light sensitivity characteristic curve for the hormones that control the circadian rhythm of the human, and is a curve having the maximum sensitivity in a circadian wavelength band. Here, the circadian wavelength band may be in the range of 450 nm to 550 nm, a main peak wavelength may be 460 nm, a full-width at half-maximum transmission (FWHM) may be in the range of 80 nm to 95 nm, and the circadian wavelength band may have an area concordance rate of 80% or more with a wavelength band of the circadian sensitivity curve.

As shown in FIG. 2, it may be confirmed that a characteristic curve of the circadian lambda filter 110 according to the embodiment of the present disclosure almost coincides with the circadian sensitivity curve (c-λ), and accordingly, the circadian lambda filter 110 may pass the external light according to the circadian sensitivity curve.

Meanwhile, a general illuminance measuring apparatus measures illuminance (lux) of the external light using a visual lambda filter (v-λ filter) that follows a visual sensitivity curve (visual lambda: v-λ), that is, a light sensitivity characteristic curve for human eyes.

According to the visual sensitivity curve, the maximum sensitivity is obtained in a wavelength band of about 550 nm to 600 nm.

However, in the general illuminance measuring apparatus following the visual sensitivity curve, different external light may have different circadian illuminance (biolux) values according to the type of external light source even though the same illuminance (lux) value is measured. This is because a luminescence spectrum varies according to the type of external light source, and when the luminescence spectrum is changed, the light sensitivity characteristic for the hormones controlling the circadian rhythm is changed.

For this reason, in order to measure the circadian illuminance (biolux), the conventional circadian illuminance measuring apparatus was using a complicated method in which an illuminance (lux) value and a luminescence spectrum of the external light source are each measured, and then the circadian action factor is calculated on the basis of the measured illuminance (lux) value and luminescence spectrum to calculate the circadian illuminance (biolux) value.

Alternatively, the circadian lambda filter 110 according to the embodiment of the present disclosure measures the circadian illuminance (biolux) by passing light having the circadian wavelength band in which the light sensitivity characteristic for the hormones that control the circadian rhythm is the maximum sensitivity, that is, the light having a wavelength band of 450 nm to 550 nm, and blocking light having a wavelength band other than 450 nm to 550 nm.

As described above, the circadian illuminance measuring apparatus 100 according to the embodiment of the present disclosure may measure the circadian illuminance (biolux) in a relatively simple method in comparison with the related art by applying the circadian lambda filter 110. Further, since additional components for calculating the circadian illuminance may be omitted, the circadian illuminance measuring apparatus 100 may be downsized, and it is possible to apply to various products at low cost.

Meanwhile, although the illuminance (lux) and the circadian illuminance (biolux) are closely related, the illuminance (lux) and the circadian illuminance (biolux) have different proportional factors depending on the color temperature. That is, there is little difference between the circadian illuminance (biolux) and the illuminance (lux) at a relatively high color temperature, and there is a great difference between the circadian illuminance (biolux) and the illuminance (lux) at a relatively low color temperature.

That is, as shown in FIG. 3, during the period from 08:00 to 18:00, since the color temperature is lowered as it goes to a later point of time even when the illuminance (lx) is constant, a circadian illuminance (blx) value becomes smaller than an illuminance (lx) value.

Thus, the circadian illuminance measuring apparatus 100 according to the embodiment of the present disclosure may more accurately measure the circadian illuminance (biolux) value in a time zone having a relatively low color temperature in comparison with the general illuminance measuring apparatus.

As shown in FIG. 4A, the circadian lambda filter 110 may include a band pass filter formed by cascading a blue pass filter and a yellow pass filter.

Here, the blue pass filter may transmit light having a wavelength band of 550 nm or less (transmittance of 50% or more) and may block light having a wavelength band of more than 550 nm (transmittance of less than 50%).

Further, the yellow pass filter may transmit light having a wavelength band of 450 nm or more (transmittance is 50% or more) and may block light having a wavelength band of less than 450 nm (transmittance is less than 50%).

Accordingly, the circadian lambda filter 110 may measure the circadian illuminance (biolux) by passing light having a wavelength band of 450 nm to 550 nm and blocking light having a wavelength band other than 450 nm to 550 nm, as a band-pass filter.

Further, FIG. 4B is a graph illustrating the characteristic curve of the circadian lambda filter 110 (for example, OP913+filter, DET36A) according to the embodiment of the present disclosure and an ideal circadian sensitivity curve ($C(\lambda)$), and as shown in FIG. 4B, it may be confirmed that the characteristic curve of the circadian lambda filter 110 shows the maximum sensitivity at a wavelength of about 450 nm, and there may be a deviation from the ideal circadian sensitivity curve ($C(\lambda)$) according to a characteristic curve of the light sensor 120 that senses the external light has passed through the circadian lambda filter 110.

Accordingly, the ideal circadian sensitivity curve may be realized by reflecting such a deviation to the circadian lambda filter 110.

The light sensor 120 senses the external light that has passed through the circadian lambda filter 110, and converts the detected external light into an analog signal (for example, a voltage value) and outputs the analog signal.

Here, the light sensor 120 may include a photodiode and a variable resistor, and may output a voltage value corresponding to a value obtained by integrating the amount of light passing through the circadian lambda filter 110 for by wavelength.

The circadian illuminance calculator 130 receives the analog signal from the light sensor 120, converts the analog signal into a digital signal, and calculates the circadian illuminance (biolux) of the external light.

Specifically, as shown in FIG. 1, the circadian illuminance calculator 130 may include a programmable gain amplifier (PGA) 131, an analog-digital converter (ADC) 132, and a controller 133.

Here, the ADC 132 converts the analog signal output from the light sensor 120 into the digital signal. In addition, the PGA 131 receives the analog signal from the light sensor 120, amplifies the analog signal, and outputs the amplified signal to the ADC 132 after varying an output gain.

Here, the output gain may be a gain value that may satisfy a range in which the analog signal received by the ADC 132 may be processed by the ADC 132.

When the analog signal received by the ADC 132 is out of the range in which the analog signal may be processed by the ADC 132, the controller 133 outputs a control signal for varying the output gain to the PGA 131.

Specifically, when the analog signal output from the light sensor 120 is out of the range in which the analog signal may be processed by the ADC 132 and becomes saturated, the PGA 131 receives the control signal from the controller 133, reduces the output gain, and outputs the analog signal.

In addition, the ADC 132 may process the analog signal in the entire range by converting the analog signal whose output gain is reduced into the digital signal.

As described above, the circadian illuminance measuring apparatus 100 according to the embodiment of the present disclosure may diagnose the circadian rhythm of the user by measuring the circadian illuminance, and may reinforce the circadian rhythm of the user according to the circadian rhythm of the user, which is diagnosed through a separate circadian reinforcement part (not shown).

That is, the disturbed circadian rhythm of the user may be corrected by adjusting the hormones that control the circadian rhythm, and diseases caused by the disturbances of the circadian rhythm, such as seasonal affective disorders, sleep disorders, depression, jet lag, and health problems associated with shift work may be treated.

For example, the circadian rhythm of the user may be well balanced by irradiating the eyes of the user with the light of the circadian wavelength band through the circadian reinforcement part (not shown) to suppress the melatonin secretion of the user in the morning time period, and thus by helping the melatonin to be easily secreted in the evening time period.

As shown in FIG. 1, the circadian illuminance measuring apparatus 100 according to the embodiment of the present disclosure may further include a display part 140 configured to display the circadian illuminance (biolux) corresponding to the digital signal converted by the ADC 132.

Thus, the user may visually confirm a current state of the circadian rhythm of the user, and correct the circadian rhythm according to the circadian rhythm state.

Further, the circadian illuminance measuring apparatus 100 according to the embodiment of the present disclosure may further include a storage 150 configured to store the circadian rhythm according to time and a reference circadian illuminance (biolux) value required according to the circadian rhythm.

Here, the controller 133 may compare the reference circadian illuminance value stored in the storage 150 with the measured circadian illuminance value, and cause the display part 140 to display a warning for reinforcing the circadian rhythm when the measured circadian illuminance value is smaller than the reference circadian illuminance value.

According to the present disclosure, circadian illuminance can be measured in a relatively simple manner by applying a circadian lambda filter, additional components for calculating the circadian illuminance can be omitted and thus a circadian illuminance measuring apparatus can be downsized, and it can be applied to various products at low cost.

Further, a circadian rhythm of a user can be diagnosed by measuring circadian illuminance, and the circadian rhythm of the user can be reinforced according to the diagnosed circadian rhythm of the user.

Effects of the present disclosure are not limited to the above-mentioned effects, and other unmentioned effects will be clearly understood by those skilled in the art from the following description.

The embodiment described in the present specification and the accompanying drawings is merely illustrative of a part of the technical ideas included in the present disclosure. Therefore, the embodiment of the present specification is not intended to limit, but is intended to illustrate the technical idea of the present disclosure, and the scope of the technical idea of the present disclosure is not limited by the embodiment. The modified examples and specific examples which could be readily inferred by a person skilled in the art within the scope of the technical ideas included in the specification and drawings of the present disclosure are to be construed as being included in the scope of the present disclosure.

What is claimed is:

1. A circadian illuminance measuring apparatus comprising:
   a circadian lambda filter configured to pass external light according to a circadian sensitivity curve;
   a light sensor configured to sense the external light has passed through the circadian lambda filter, convert the external light into an analog signal, and output the analog signal; and
   a circadian illuminance calculator configured to convert the analog signal into a digital signal to calculate circadian illuminance of the external light,
   wherein the circadian sensitivity curve is a light sensitivity characteristic curve for a hormone that controls a circadian rhythm, and is a curve having the maximum sensitivity in a circadian wavelength band.

2. The circadian illuminance measuring apparatus of claim 1, wherein the hormone that controls the circadian rhythm is melatonin.

3. The circadian illuminance measuring apparatus of claim 1, wherein the circadian wavelength band is in a range of 450 nm to 550 nm.

4. The circadian illuminance measuring apparatus of claim 1, wherein a full-width at half-maximum transmission (FWHM) of the circadian wavelength band is in a range of 80 nm to 95 nm.

5. The circadian illuminance measuring apparatus of claim 1, wherein the circadian wavelength band has an area concordance rate of 80% or more with a wavelength band of the circadian sensitivity curve.

6. The circadian illuminance measuring apparatus of claim 1, wherein the circadian lambda filter is a band pass filter formed by cascading a blue pass filter and a yellow pass filter.

7. The circadian illuminance measuring apparatus of claim 1, further comprising a display part configured to display the circadian illuminance corresponding to the digital signal.

8. The circadian illuminance measuring apparatus of claim 1, wherein the circadian illuminance calculator includes a programmable gain amplifier configured to receive the analog signal from the light sensor, amplify the analog signal, and output the amplified signal after varying an output gain.

9. The circadian illuminance measuring apparatus of claim 8, wherein the circadian illuminance calculator further includes an analog-digital converter configured to receive the analog signal amplified by the programmable gain amplifier, and convert the analog signal into the digital signal.

10. The circadian illuminance measuring apparatus of claim 9, wherein the output gain is a gain value satisfying a range in which the analog signal received by the analog-digital converter is processed by the analog-digital converter.

11. The circadian illuminance measuring apparatus of claim 8, wherein the circadian illuminance calculator further includes a controller configured to output a control signal for varying the output gain to the programmable gain amplifier when the analog signal received by the analog-digital converter is out of the range in which the analog signal is processed by the analog-digital converter.

* * * * *